Figure 1:
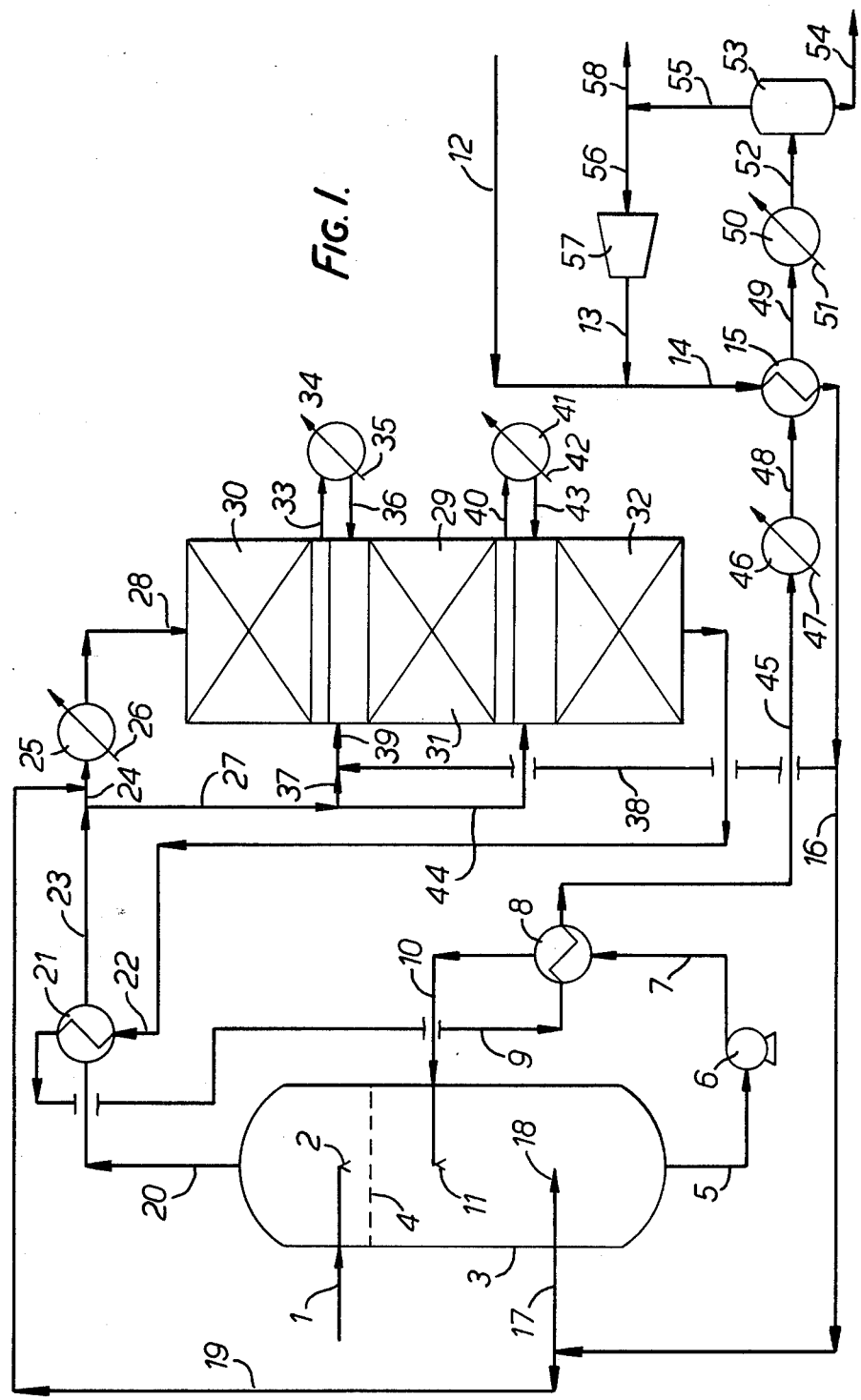

United States Patent [19]

Bradley et al.

[11] 4,451,677

[45] May 29, 1984

[54] MULTISTAGE ALDEHYDE HYDROGENATION

[75] Inventors: Michael W. Bradley, Marton; Andrew G. Hiles, Sutton; John W. Kippax, Ingleby Greenhow, all of England

[73] Assignee: Davy McKee (London) Limited, London, England

[21] Appl. No.: 409,931

[22] Filed: Aug. 20, 1982

Related U.S. Application Data

[63] Continuation-in-part of Ser. No. 294,520, Aug. 20, 1981, abandoned.

[51] Int. Cl.³ .............................................. C07C 29/14
[52] U.S. Cl. .................................................... 568/881
[58] Field of Search ........................................ 568/881

[56] References Cited

U.S. PATENT DOCUMENTS 2,549,416 4/1951 Brooks ................................. 568/881
2,771,493 11/1956 Jacks et al. ........................... 568/881

FOREIGN PATENT DOCUMENTS 8767 3/1980 European Pat. Off. ............ 568/881
765972 1/1957 United Kingdom ................ 568/881
781405 8/1957 United Kingdom ................ 568/881

OTHER PUBLICATIONS

Vener, "Chemical Engineering", Jul. 1955, pp. 204, 205.

Primary Examiner—J. E. Evans
Attorney, Agent, or Firm—Bernard, Rothwell & Brown

[57] ABSTRACT

A multi-stage hydrogenation process for hydrogenating a vaporous aldehyde to a corresponding alcohol utilizing a plurality of adiabatic catalytic stages is described. Hydrogenation is allowed to occur substantially completely and adiabatically in each stage. Further vaporous aldehyde or a mixture of hydrogen and vaporous aldehyde is added to the essentially aldehyde-free mixture exiting each catalytic stage prior to entry to the next stage.

37 Claims, 3 Drawing Figures

MULTISTAGE ALDEHYDE HYDROGENATION

This application is a continuation-in-part of application Ser. No. 294,520 filed Aug. 20, 1981, now abandoned.

This invention relates to a hydrogenation process, more particularly to a process for vapour phase hydrogenation of an aldehyde to the corresponding alcohol.

Hydrogenation of an aldehyde to the corresponding alcohol can be effected by passage of a vaporous stream comprising the aldehyde and a hydrogen-containing gas over a solid catalyst. Such hydrogenation reactions are practised commercially on a large scale, for example in the production of n-butanol from n-butyraldehyde and in the production of 2-ethylhexanol from 2-ethylpropylacrolein (2-ethylhex-2-enal).

The aldehyde hydrogenation reaction is highly exothermic and it is conventional practice to effect the reaction in cooled tubular reactors and to use an excess of hydrogen, which acts as a heat sink and helps to control the temperature rise in the reactor. A process of this type has been described, for example, in European Patent Publication No. 0 008 767 (European patent application No. 79103181.8 filed Aug. 28, 1979 by Union Carbide Corporation).

Commercial 2-ethylpropylacrolein hydrogenation plants are generally operated at a high hydrogen:aldehyde molar ratio. Typically this ratio is about 40:1 when using cooled tubular reactors. The excess hydrogen is recycled after alcohol product recovery.

The reaction can be carried out adiabatically which has the advantage that an adiabatic reactor is much cheaper than cooled a cooled tubular reactor. However under adiabatic reaction conditions even higher hydrogen: aldehyde molar ratios, typically in excess of 50:1, must be used. Again excess hydrogen may be recycled after alcohol product recovery. The use of such high hydrogen:aldehyde molar ratios means, however, that a correspondingly large gas recycle compressor must be used, thus increasing capital and running costs.

It has been proposed in U.S. Pat. No. 2,771,493 and in British Patent Specification No. 765,972 to effect hydrogenation of aldehydes in a hydrogenation oven in the form of a quench reactor. In the plant of FIG. 1 of each of these prior specifications a mixture of aldehyde vapour and hydrogen that has been preheated in a fired coil is admitted to the inlet end of the reactor which is divided into alternate reaction and cooling zones, whilst a high pressure stream of relatively cool hydrogen is continuously injected into each of the cooling zones in order to moderate the temperature of the reaction mixture and prevent temperature runaways occurring in the subsequent reaction zone. Hence a part only of the aldehyde supplied to the inlet end of the reactor is hydrogenated in each reaction zone. Although the plant is provided with strategically placed instruments to control the high pressure hydrogen stream used for quench purposes with the aim that, if the coil outlet temperature should for any reason rise to a predetermined value, the relatively cool hydrogen can be instantly and automatically admitted to the coil outlet to lower the temperature below this maximum, thereby to assure that the hydrogenation oven inlet temperatures can never rise to a dangerously high level, yet nevertheless there is a risk of the control equipment failing with the result that danger of temperature runaways cannot be entirely ruled out in this form of plant.

U.S. Pat. No. 2,549,416 describes vapour phase reduction of 3,5,5-trimethylhexanal over a catalyst comprising reduced copper plus zinc oxide in a tubular reactor to yield 3,5,5-trimethylhexanol-1.

It would be desirable to provide a way of effecting vapour phase hydrogenation of aldehydes which offers the capital savings associated with the use of an adiabatic reactor and the possibility of utilising lower than normal hydrogen:aldehyde ratios and hence a smaller recycle compressor, thereby enabling further savings in capital and running costs to be made.

The present invention accordingly seeks to provide an improved process for heterogeneous catalytic vapour phase hydrogenation of aldehydes to the corresponding alcohols which utilises a plurality of adiabatic reactors and in which significantly lower than usual overall hydrogen:aldehyde molar ratios can be used in the vapour stream being passed over the catalyst, hence enabling smaller than usual gas recycle compressors to be used.

According to the invention there is provided a process for hydrogenating an aldehyde to a corresponding alcohol which comprises providing a plurality of adiabatically operated catalytic stages arranged one after another, including a first catalytic stage and a final catalytic stage, each catalytic stage containing a charge of a hydrogenation catalyst effective for vapour phase catalytic hydrogenation of aldehydes, supplying to the first catalytic stage a first vaporous mixture comprising vaporous aldehyde and excess hydrogen, supplying to the, or to each, other catalytic stage a vaporous mixture comprising (a) unreacted hydrogen and corresponding alcohol recovered from the preceding catalytic stage and (b) further aldehyde, the vaporous mixture supplied to each catalytic stage being in each case at a temperature at least as high as the threshold temperature for the hydrogenation reaction, allowing catalytic hydrogenation to occur substantially adiabatically in each catalytic stage, thereby to convert to corresponding alcohol substantially all aldehyde supplied to that stage, and recovering from the final catalytic stage a substantially aldehyde-free vaporous reaction mixture containing corresponding alcohol.

The invention thus provides a process for vapour phase hydrogenation of an aldehyde to the corresponding alcohol which comprises providing a catalytic hydrogenation zone comprising n catalytic stages in series, where n is an integer of at least 2, each catalytic stage containing a charge of a hydrogenation catalyst effective for vapour phase catalytic hydrogenation of aldehydes, supplying to the first catalytic stage a first vaporous mixture comprising excess hydrogen and the aldehyde at a first predetermined hydrogen:aldehyde molar ratio and at a first temperature which is equal to, or is in excess of, the threshold temperature for the hydrogenation catalyst thereof, allowing catalytic hydrogenation to occur substantially adiabatically in each catalytic stage, thereby to effect hydrogenation to corresponding alcohol of substantially all aldehyde supplied to that stage, supplying vaporous product mixture from the, or from each, mth catalytic stage in the series, where m is an integer equal to or less than (n−1), to the corresponding (m+1)th catalytic stage in the series, supplying also further vaporous aldehyde to the, or to each, (m+1)th catalytic stage to form, together with the vaporous product mixture from the mth catalytic stage, a vaporous mixture having a predetermined hydrogen:aldehyde molar ratio which may be the same as, or may be different from, the first predetermined ratio or the corresponding molar ratio for the vaporous mixture supplied to any other stage, controlling the inlet temperature to the, or to each, (m+1)th catalytic stage to a predetermined temperature which is equal to, or is in excess of, the threshold temperature for the catalyst, and recovering from the nth catalytic stage a substantially aldehyde-free final vaporous product mixture containing the corresponding alcohol.

The integer n may be 2, 3, 4, 5, 6 or more. However, in a particularly preferred process n represents 3, so that the process comprises providing a catalytic hydrogenation zone comprising first, second and third catalytic stages in series, each catalytic stage containing a charge of a hydrogenation catalyst effective for vapour phase catalytic hydrogenation of aldehydes, supplying to the first catalytic stage a first vaporous mixture comprising excess hydrogen and the aldehyde at a first predetermined molar ratio at a first inlet temperature which is equal to, or is in excess of, the threshold temperature for the hydrogenation catalyst, allowing catalytic hydrogenation to occur substantially completely and substantially adiabatically in the first catalytic stage, supplying first product mixture comprising corresponding alcohol and unreacted hydrogen from the first catalytic stage to the second catalytic stage, supplying also to the second catalytic stage further vaporous aldehyde to form, together with the first product mixture, a second vaporous mixture containing hydrogen and vaporous aldehyde and having a predetermined second hydrogen:aldehyde molar ratio which may be equal to, or may be different from, the first ratio, controlling the inlet temperature to the second catalytic stage to a predetermined temperature which is equal to, or is in excess of, the threshold temperature of the catalyst, allowing catalytic hydrogenation to occur substantially completely and substantially adiabatically in the second catalytic stage, supplying second product mixture comprising corresponding alcohol and unreacted hydrogen from the second catalytic stage to the third catalytic stage, supplying also to the third catalytic stage further vaporous aldehyde, to form together with the second product mixture, a third vaporous mixture containing hydrogen and vaporous aldehyde and having a predetermined third hydrogen:aldehyde molar ratio which may be equal to, or may be different from, the first and/or second ratios, controlling the inlet temperature to the third catalytic stage to a predetermined equal to or in excess of the threshold temperature of the catalyst, allowing catalytic hydrogenation to occur substantially completely and substantially adiabatically in the third catalytic stage, and recovering from the third catalytic stage a third product mixture containing the corresponding alcohol.

In the process of the invention the vaporous product mixture from each catalytic stage comprises corresponding alcohol (e.g. 2-ethylhexanol when the aldehyde is 2-ethylpropylacrolein or n-butanol when the aldehyde is n-butyraldehyde) and unreacted hydrogen plus inerts, and is substantially aldehyde-free. Vaporous aldehyde is introduced into the vaporous product mixture recovered from the first and any other catalytic stage, up to and including the penultimate catalytic stage, prior to introduction of the resulting vaporous reactant mixture into the next catalytic stage. In an especially preferred process aldehyde alone is thus introduced into the vaporous product mixture from the preceding stage to form the vaporous reactant mixture introduced into the or each catalytic stage downstream from the first catalytic stage.

According to an alternative preferred procedure a supplementary mixture comprising further hydrogen and vaporous aldehyde is introduced into the respective vaporous product mixture from the preceding catalytic stage to form the respective vaporous reactant mixture that is introduced into the or each catalytic stage downstream from the first catalytic stage. The invention further embraces processes in which there are several catalytic stages downstream from the first catalytic stage and vaporous aldehyde alone is introduced into the respective vaporous product mixture from the preceding catalytic stage prior to introduction into at least one of those downstream catalytic stages, whilst a supplementary mixture comprising further hydrogen and vaporous aldehyde is introduced into the respective vaporous product mixture from the preceding catalytic stage prior to introduction into at least one other of those downstream catalytic stages.

When a supplementary mixture comprising further hydrogen and vaporous aldehyde is so introduced into the respective vaporous product mixture prior to introduction to one or more of the catalytic stages downstream from the first catalytic stage, the hydrogen:aldehyde molar ratio of such a supplementary mixture may be the same as, or may be different from, the first predetermined molar ratio (i.e. the molar ratio for the vaporous mixture introduced to the first catalytic stage) or the corresponding ratio for the supplementary mixture supplied to any other stage.

The process of the invention may be conducted with inter-cooling between successive catalytic stages. Such inter-cooling may be provided between the first and second catalytic stages, if there are only two catalytic stages, or between one or more successive pairs of catalytic stages, if there are more than two catalytic stages. There may be provision for inter-cooling between each successive pair of stages. Hence the vaporous product mixture from the, or from at least one, mth catalytic stage (preferably the vaporous product mixture from the or each mth catalytic stage) may be cooled prior to being supplied to the corresponding (m+1)th catalytic stage. Such inter-cooling may occur before or after admixture of the vaporous product mixture from the mth catalytic stage with the further vaporous aldehyde or with the supplementary mixture of hydrogen and vaporous aldehyde for the (m+1)th catalytic stage. Whether or not it is necessary or desirable to include provision for inter-cooling will depend upon the desired inlet temperature to the next succeeding stage, on the exit temperature from the preceding stage, on the temperature of the further vaporous aldehyde or of the supplementary mixture of hydrogen and vaporous aldehyde supplied to that next succeeding stage, and on the amounts of such further aldehyde or of the supplementary mixture of further hydrogen and vaporous aldehyde relative to the amount of vaporous product mixture exiting the preceding stage.

Within each catalytic stage the hydrogenation reaction proceeds adiabatically and essentially to completion. Hence the concentration of unreacted aldehyde in the vaporous product mixture exiting each catalytic stage is very small.

The hydrogen supplied to the first and to any succeeding catalytic stage in the form of a substantially pure hydrogen gas or as a hydrogen containing gas.

The process is conducted so that an excess of hydrogen is present in each catalytic stage over and above the stoichiometric quantity of hydrogen required to reduce the quantity of aldehyde supplied to that catalytic stage. For a saturated aldehyde the stoichiometric quantity corresponds to 1 mole of hydrogen per mole of aldehyde; for unsaturated aldehydes an extra mole of hydrogen is required for each reducible unsaturated double bond and an extra 2 moles of hydrogen for each reducible unsaturated triple bond.

The first predetermined hydrogen:aldehyde molar ratio may vary within wide limits, e.g. from about 2:1 to about 100:1 or more. Usually, however, it will be selected to lie within the range of from about 5:1 to about 75:1. The molar ratio of any supplementary mixture of further hydrogen and vaporous aldehyde supplied to the second and to any subsequent catalytic stage may be substantially equal to the first predetermined ratio. Usually, however, it will be preferred to supply the second and any succeeding catalytic stage with a supplementary mixture of further hydrogen and aldehyde at a lower hydrogen:aldehyde molar ratio than the first predetermined ratio. If desired, the respective molar ratio may decrease from stage to stage through at least the initial catalytic stages of the series. This means that, even if a higher hydrogen:aldehyde molar ratio is used in the first catalytic stage than would be used in a conventional tubular reactor plant, the overall hydrogen:aldehyde ratio for all the stages taken together can be reduced by appropriate selection of the molar ratio of the supplementary mixture of further hydrogen and aldehyde supplied to the second and to any subsequent catalytic stage. Hence a smaller than usual gas recycle compressor may be required by selection of appropriate conditions in the process of the invention, thus leading to significant savings in capital costs and in running costs. At all events the hydrogen:aldehyde molar ratios will normally be chosen so as to limit the adiabatic temperature rise in each stage within the safe operating conditions of the catalyst.

The aldehyde may be any vaporisable aldehyde or mixture of aldehydes that is susceptible to catalytic hydrogenation. Preferebly, however, it contains from 1 to about 20 carbon atoms. As examples of aldehydes which can be used in the present invention there may be mentioned acetaldehyde, propionaldehyde, crotonaldehyde, n- and iso-butyraldehydes, n-pentanal, 2-methylbutanal, 2-ethyl-3-propylacrolein, 2-ethylhexanal, $C_{10}$-"oxo"-aldehydes (e.g. 2-propyl-3-butylacrolein), and furfural, as well as mixtures thereof. The corresponding alcohols to these examples of aldehydes are respectively, ethanol, n-propanol, n-butanol, n- and iso-butanol, n-amyl alcohol, 2-methylbutanol, 2-ethylhexanol, 2-ethylhexanol, $C_{10}$-"oxo"-alcohols (e.g. 2-propylheptanol), and furfuryl alcohol. The aldehyde may be in a substantially pure state or admixed with a component or components other than an aldehyde, e.g. the corresponding alcohol. A mixture of aldehydes may be used, e.g. a mixture of isomeric aldehydes, such as a mixture of n- and iso-aldehydes.

The process of the invention may be operated at atmospheric pressure or at sub-atmospheric pressure but is preferably carried out at super-atmospheric pressure, for example a pressure in the range of from about 1 kg/cm$^2$ absolute (about 14 psia) up to about 21 kg/cm$^2$ absolute (about 300 psia) or higher. The choice of pressure will usually be determined to some extent by the volatility of the aldehyde to be hydrogenated and the limits of operating temperature of the selected catalyst. Conveniently the reaction pressure is substantially the same in each catalytic stage but different pressures may prevail in different catalytic stages if desired.

The inlet temperature to each catalytic stage must be selected to lie above the dew point for the composition at the inlet to that catalytic stage and is at least as high as the threshold temperature for the catalyst. Such threshold temperature may vary from catalyst to catalyst. For a catalyst of the type whose use is claimed in the afore-mentioned European Patent Publication No. 0 008 767, for example, the inlet temperature to each catalytic stage preferably lies in the range of from about 100° C. to about 180° C. Control of the inlet temperature to the second and any subsequent catalytic stage can be achieved by appropriate selection of the ratio between the rate of supply of aldehyde or of the supplementary mixture of further hydrogen and vaporous aldehyde to that stage of supply of vaporous product mixture from the preceding catalytic stage and by appropriate selection of the temperatures of these two streams. As to the temperatures of the streams of aldehyde or of the supplementary mixture or mixtures of further hydrogen and vaporous aldehyde supplied to the second and any subsequent stage, these may vary from stage to stage (if there are 3 or more stages).

Within each catalytic stage catalytic hydrogenation occurs substantially adiabatically. Care should be taken in operating the process not to allow the temperature to rise within any catalytic stage to such a high temperature that catalyst activity is destroyed or impaired or that the level of by-product formation becomes unacceptably high. Control of maximum "hot spot" temperatures can be achieved by controlling the hydrogen:aldehyde ratio of the vaporous reactant mixture supplied to each catalytic stage and by controlling the inlet temperature thereto. Moderation of the maximum "hot spot" temperature of a particular catalyst bed can be achieved, for example, by increasing the hydrogen:aldehyde ratio. When using a catalyst of the type described in the afore-mentioned European Patent Publication No. 0 008 767 it is preferred to operate so that the exit temperature, and the temperature of any "hot spot," does not exceed about 260° C. and preferably does not exceed about 230° C.

The hydrogenation catalyst may be any catalyst suitable for vapour phase hydrogenation of aldehydes. As examples of suitable commercially available catalyst there may be mentioned copper chromite; cobalt compounds; nickel; nickel compounds which may contain small amounts of chromium or another promoter; and mixtures of copper and nickel and/or chromium. The nickel compounds generally are deposited on support materials such as alumina and kieselguhr. The use of a reduced mixture of the oxides of copper and zinc is described in U.S. Pat. No. 2,549,416, whilst U.S. Pat. No. 4,052,467 uses a reduced mixture of oxides or hydroxides of copper and zinc to hydrogenate an aldehyde feed containing ring-type sulphur compounds. According to European Patent Publication No. 0 008 767 the use of a reduced mixture of CuO and ZnO under specified reaction conditions gives rise to negligible formation of by-products, such as ethers, and hydrocarbon gases and also to small amounts only of "heavies" formation (such as esters). Hence the use of such a reduced mixture of CuO and ZnO as hydrogenation catalyst is preferred in the practice of the present invention. Such a catalyst may contain minor amounts of other materials such as chloride, sodium, sulphur, and aluminium oxide and may be prepared by any of the methods disclosed in the afore-mentioned European Patent Publication No. 0 008 767. An inert carrier material may be included in the catalyst composition which is generally formed into pellets, tablets, or any other shape, prior to use, by conventional techniques.

The alcohol product from the hydrogenation zone may be separated from the unreacted excess hydrogen and other gaseous constituents, e.g. inerts, by condensation, the excess hydrogen being compressed and recycled to the hydrogenation zone. The crude alcohol may be further purified in conventional manner by fractional distillation. Any unconverted aldehyde possibly together with any intermediate hydrogenation products (e.g. 2-ethylhex-2-enol in the production of 2-ethylhexanol from 2-ethylpropylacrolein), may be separated from the reaction product and recycled. A gaseous bleed stream may be taken from the recycled gas in order to control the build up of inerts in the recycled gas.

As pointed out above, further aldehyde alone may be admixed with the vaporous mixture exiting one or more of the catalytic stages prior to introduction into the next succeeding catalytic stage. In this case it will usually be preferred to cool the vaporous mixtures from the preceding stage from its exit temperature to a temperature intermediate that exit temperature and room temperature prior to passage through an aldehyde vaporisation zone. In this way byproduct formation in the aldehyde vaporisation zone may be minimised. If the temperature in the aldehyde vaporisation zone is excessively high, undesirably high amounts of by products, such as "heavies" formed by aldehyde self-condensation reactions followed, possibly, by dehydration, may otherwise be produced. Depending on the temperature conditions prevailing in the aldehyde vaporisation zone it may be necessary to heat the resulting aldehyde-containing vaporous mixture somewhat prior to entry to the next succeeding catalytic stage.

The vaporous aldehyde and the hydrogen or hydrogen-containing gas to form any supplementary mixture may be supplied as separate streams to each catalytic stage but are preferably pre-mixed prior to entry to the respective catalytic stage. Heat for vaporising the aldehyde, which is normally a liquid, may be provided by indirect heat exchange with a suitable source of heat, e.g. steam or hot product gases from the final catalytic stage. Hydrogen or hydrogen-containing gas may be passed through the aldehyde vaporisation zone so as to entrain the aldehyde vapour therein. The resulting aldehyde vapour/hydrogen mixture may be supplied as such to one or more of the catalytic stages or may be further diluted with hydrogen or hydrogen-containing gas prior to admission thereto. Preferably the temperature within the or each aldehyde vaporisation zone is maintained at as low a temperature as possible, consistant with achieving the desired rate of aldehyde vaporisation, to as to minimise formation of by-product "heavies," such as self-condensation products of the aldehyde and/or dehydration products thereof.

In a preferred form of the process hydrogen or hydrogen-containing gas is passed through the aldehyde vaporisation zone so as to produce a supplementary mixture with a hydrogen:aldehyde molar ratio appropriate for supply to the second and/or a subsequent catalytic stage, whilst the desired predetermined hydrogen:aldehyde molar ratio for the mixture to be admitted to the first catalytic stage is obtained by appropriate dilution with further hydrogen or hydrogen-containing gas. If desired, the hydrogen/aldehyde mixture from the aldehyde vaporisation zone may be admitted to the final catalytic stage whilst the mixture for the first catalytic stage and the supplementary mixture for the or each intermediate catalytic stage is obtained by appropriate dilution with further hydrogen or hydrogen-containing gas.

The process of the invention may be operated with a substantially pure hydrogen gas or with a hydrogen-containing gas which may be made up at least in part of recycled gas. When using such recycled gas the hydrogen-containing gas preferably contains at least about 40 mole %, more preferably at least about 70 mole %, hydrogen with the balance comprising gaseous inerts such as nitrogen and/or methane and small amounts of inert gases, e.g. argon. The gas used as make up hydrogen-containing gas preferably comprises at least about 90 mole %, more preferably at least about 95 mole %, hydrogen with the balance comprising gaseous inerts.

The catalytic hydrogenation zone may comprise a single reactor vessel divided into the individual catalytic stages, optionally with external or internal cooling between successive stages, or may comprise a plurality of vessels connected in series, optionally with interstage cooling.

Figure 2:
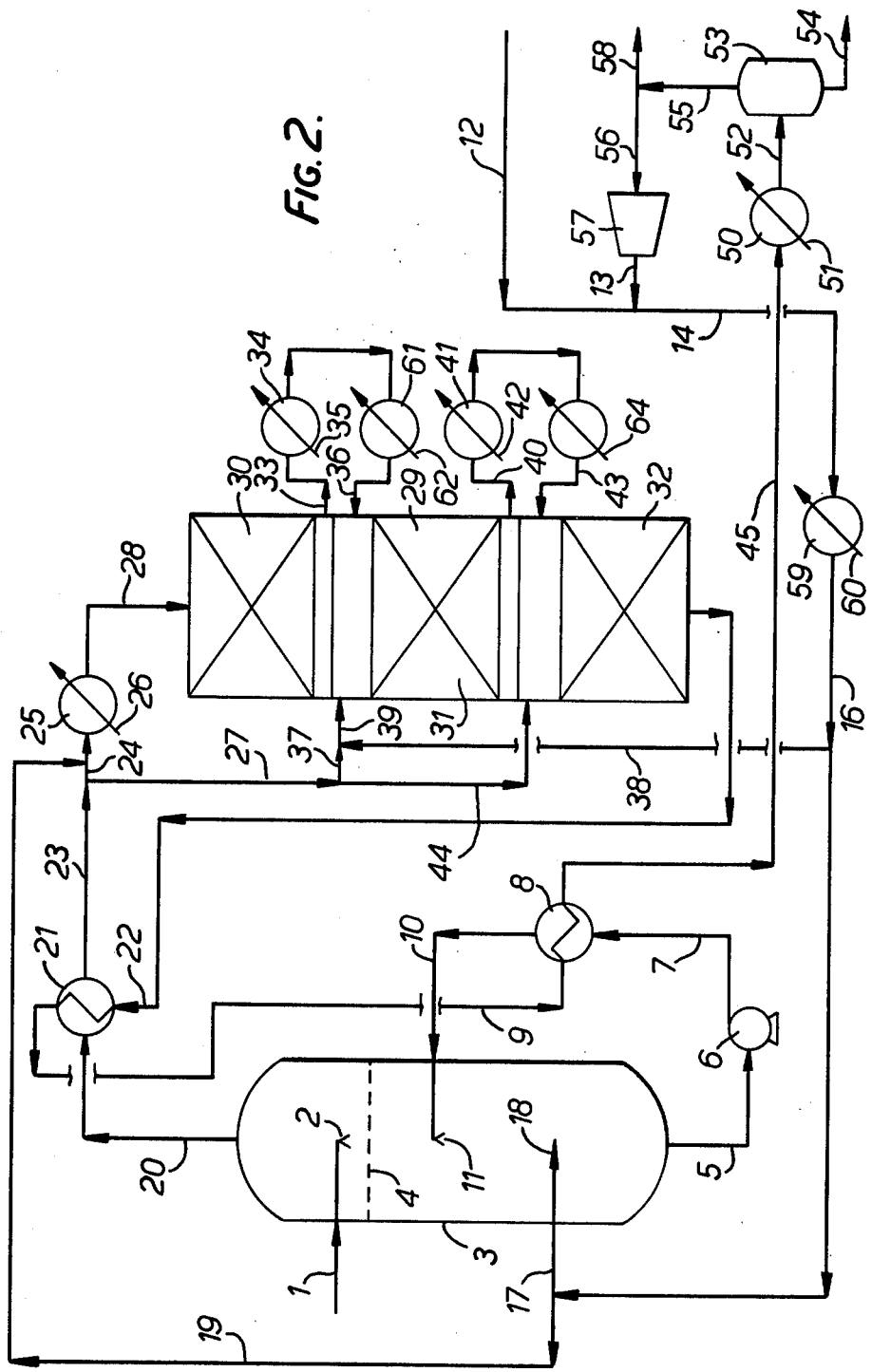
Figure 3:
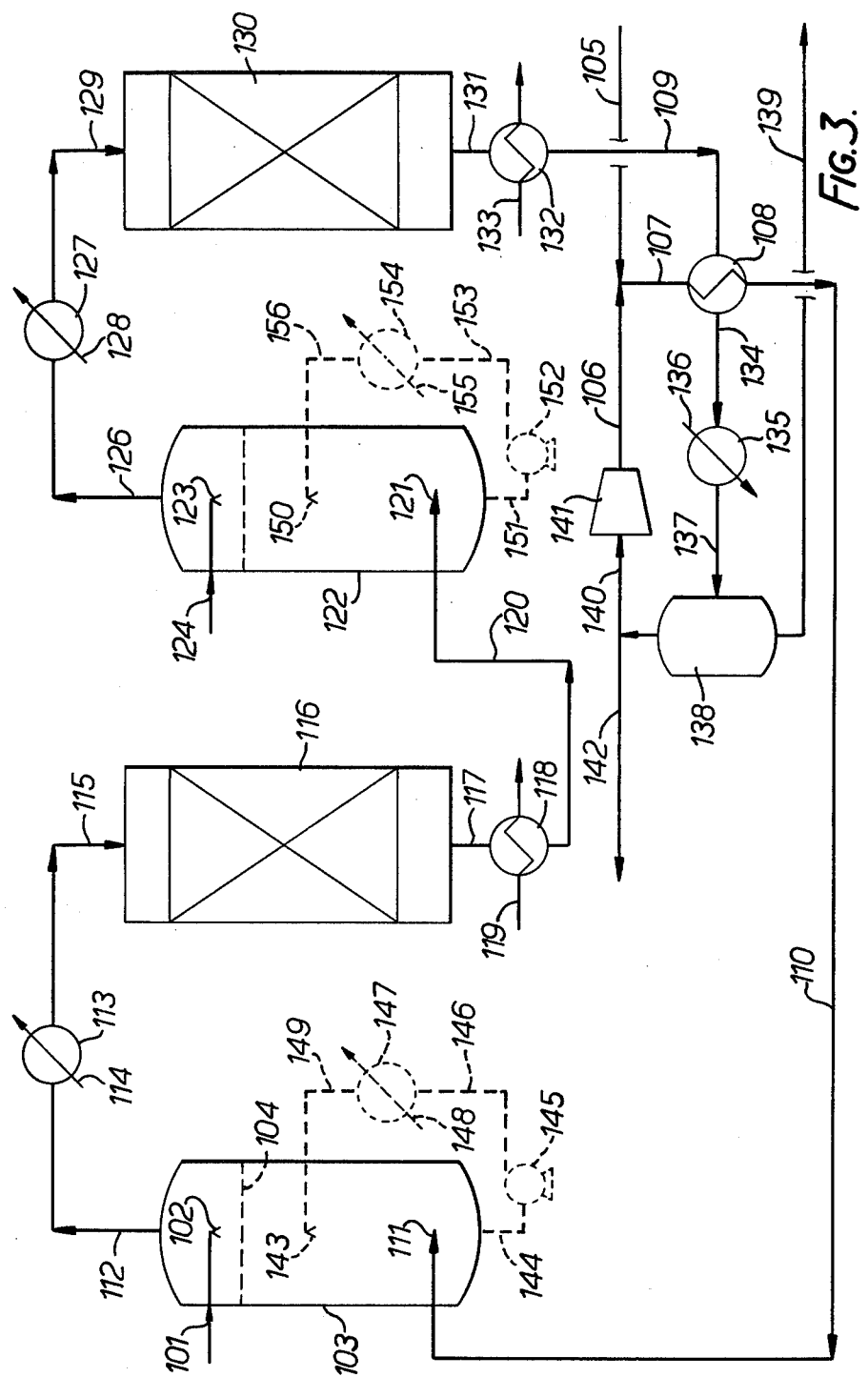

In order that the invention may be clearly understood and readily carried into effect a number of forms of process in accordance with the invention, and corresponding forms of apparatus in which such processes can be effected, will now be described, by way of example only, with reference to the accompanying diagrammatic drawings in which:

FIGS. 1 to 3 are flow sheets of different forms of heterogeneous catalytic vapour phase aldehyde hydrogenation plant.

Referring to FIG. 1 of the drawings, which illustrates a plant for the production of 2-ethylhexanol, the aldehyde 2-ethylpropylacrolein is supplied as a liquid via line 1 to a spray nozzle 2 mounted in a vaporiser column 3 which is maintained at about 5.27 kg/cm$^2$ absolute (75 psia) and is provided with a distribution tray 4. Liquid aldehyde collects in the bottom of vaporiser column 3 and is removed through line 5 by means of pump 6 which delivers it via line 7 to heat exchanger 8. The liquid aldehyde is raised to boiling point in heat exchanger 8 by indirect heat exchange with hot reaction product gases in line 9 and passes on via line 10 to a further spray nozzle 11 in vaporiser column 3.

Make-up hydrogen-containing gas is supplied by way of line 12 and is mixed with recycle gas from line 13 before passing on by way of line 14 to heat exchanger 15 in which it is preheated. The resulting preheated hydrogen-containing gas is then fed through line 16, a part being passed through line 17 to sparger 18 in vaporiser column 3, whilst another part is withdrawn in line 38 and the remainder passes on through line 19.

A vaporous mixture of aldehyde vapour and hydrogen-containing gas, comprising a 38:1 H$_2$:aldehyde molar ratio mixture plus inerts, is removed from vaporiser column 3 through line 20. This is heated further in heat exchanger 21 by indirect heat exchange with hot reaction product gases in line 22. Downstream from the heat exchanger 21 the stream of hot vaporous reactant mixture in line 23 is divided, a fraction thereof passing on through line 24 and being mixed with the hydrogen-containing gas in line 19 before passing to heat exchanger 25 in which the resulting hydrogen-enriched vaporous mixture is heated to the desired inlet temperature for the first catalytic stage of the hydrogenation zone (128° C.) by means of indirect heat exchange with steam supplied through line 26. The remainder of the vaporous mixture from line 23 passes on through line 27 for feeding to the second and subsequent catalytic stages of the hydrogenation zone as will be described further below.

The hydrogen-enriched vaporous mixture supplied from heat exchanger 25 in line 28 comprises a 53:1 $H_2$:aldehyde molar ratio mixture plus inerts, and is fed to a three-bed adiabatic reactor 29 containing a charge of aldehyde hydrogenation catalyst, for example a catalyst of the type claimed in the afore-mentioned European Patent Publication No. 0 008 767. The catalyst is divided into three beds 30, 31 and 32 arranged in series. Hydrogenation of aldehyde occurs adiabatically and substantially quantitatively in each catalyst bed 30, 31 and 32. The vaporous product mixture exiting first bed 30 is essentially aldehyde-free and passes by way of line 33 to a first interstage cooling stage 34 supplied with boiler feed water in line 35; the resulting cooled mixture is returned to the reactor 29 in line 36 at a temperature of 156° C., and is mixed, inside or outside reactor 29, with a "cold shot" of vaporous mixture. This "cold shot" is formed by mixing vaporous reactant mixture taken from line 27 in line 37 with further hydrogen containing gas supplied from line 16 through line 38. The resulting mixture, which comprises a 42:1 $H_2$:aldehyde molar ratio mixture plus 2-ethylhexanol vapour and inerts, is fed via line 39 as a "cold shot" at a temperature of 121° C. into second bed 31. The hot vaporous product mixture exiting second bed 31 is essentially aldehyde-free and then passes by way of line 40 to a second interstage cooling stage 41, supplied with boiler feed water in line 42, and returns to the reactor 29 at a temperature of 156° C. by way of line 43, prior to mixing inside or outside reactor 29 with a further "cold shot" of vaporous mixture from line 27, which is supplied by way of line 44, and prior to passage through third catalyst bed 32. The vaporous mixture in line 44 has an $H_2$:aldehyde molar ratio of 38:1 and is at a temperature of 122° C. The final vaporous product mixture exiting third catalyst bed 32 is essentially aldehyde-free and passes on to heat exchanger 21 in line 22 and gives up heat therein to the incoming vaporous mixture in line 20. From heat exchanger 21 the final vaporous product mixture flows on in line 9 to heat exchanger 8 and gives up further heat to the liquid aldehyde in line 7. The vaporous product mixture then flows on in line 45. Further heat is removed from the vaporous product mixture in boiler 46 which is used to raise steam from boiler feed water in line 47. From boiler 46 the final vaporous product mixture passes on in line 48 to heat exchanger 15, in which the mixture of make up and recycled hydrogen-containing gas is preheated, and thence in line 49 to a final stage cooler 50 supplied with coolant water in line 51. The resulting cooled mixture in line 52 passes to a knock out pot 53 whence crude liquid product alcohol, i.e. crude 2-ethylhexanol, is removed in line 54. Uncondensed gases pass by way of lines 55 and 56 to a gas recycle compressor 57 which supplies line 13. A purge gas stream is taken in line 58 in order to control the $H_2$: "inerts" molar ratio at approximately 4:1. The "inerts" are mainly nitrogen, other inert gases and possibly also methane, such "inerts" being present as impurities in the make-up hydrogen containing gas supplied by way of line 12.

Compared with a conventional plant of similar production capacity using a tubular reactor or, more usually, several tubular reactors, the capital costs of the plant of FIG. 1 are significantly reduced since it utilises adiabatic stages which can be incorporated in a single reactor vessel. Such a vessel is much cheaper than one or more tubular reactors which are more complex to fabricate and must be constructed of more expensive materials than adiabatic reactor vessels. In comparison with a plant using a single bed adiabatic reactor, the plant of FIG. 1 uses a significantly lower overall gas recycle ratio, thus offering corresponding savings in capital and running costs.

In FIG. 2 the same reference numerals are indicated as in FIG. 1 to denote like parts. However, whereas the plant of FIG. 1 has been designed with a view to minimising catalyst volume, that of FIG. 2 has been designed with the intention of minimising the gas recycle rate.

In FIG. 2 the arrangements for supplying feed aldehyde, 2-ethylpropylacrolein, in line 1 and for vaporising it in vaporiser column 3 are the same as those for the plant of FIG. 1. However, heat exchanger 15 is omitted and instead the incoming mixture of make up and recycled hydrogen-containing gas in line 14 is heated in heat exchanger 59 by means of steam supplied in line 60. Additionally further interstage cooling is provided between the first and second catalyst beds 30 and 31 as well as between the second and third catalyst beds 31 and 32. This additional interstage cooling takes the form of cooler 61, which is supplied with cooling water in line 62, in line 33 and of a corresponding cooler in line 40, i.e. cooler 63, fed with cooling water in line 64. As in the plant of FIG. 1 hydrogenation of aldehyde occurs substantially completely and adiabatically in each of the catalyst beds 30, 31 and 32.

Downstream from the adiabatic reactor 29 the arrangements for cooling the final vaporous product mixture from the third catalyst bed are different from those of FIG. 1. Thus boiler 44 is omitted (as well as heat exchanger 15). Otherwise the plant of FIG. 2 is essentially the same as that of FIG. 1.

The vaporous mixture in line 28 of the plant of FIG. 2 is at a pressure of about 5.27 kg/cm² absolute (75 psia) and at a temperature of 128° C. and has an $H_2$:aldehyde molar ratio of 53:1. The mixture in line 36 is at a temperature of 133° C. The $H_2$:aldehyde molar ratio of the mixture in line 39 is 18.5:1. The mixture in line 43 is at a temperature of 144° C.; the "cold shot" in line 44 has an $H_2$:aldehyde molar ratio of 18:1. As before the $H_2$:inerts ratio is about 4:1.

In each of the plants of FIGS. 1 and 2 the conversion of aldehyde, 2-ethylpropylacrolein, to the corresponding alcohol, 2-ethylhexanol, is essentially quantitative.

The overall $H_2$:aldehyde molar ratio for the plant of FIG. 2 is 26.9:1. A plant with a single adiabatic catalytic stage would require an $H_2$:aldehyde molar ratio of approximately 55:1. A plant of tubular reactor design would require an $H_2$:aldehyde ratio of approximately 40:1. Thus, compared with a conventional plant of tubular or adiabatic reactor design of similar capacity the plant of FIG. 2 can be operated at an overall $H_2$:aldehyde molar ratio that is significantly smaller than that required for the conventional plant, hence leading to savings in the size of the gas recycle compressor and its power consumption. In particular the plant of FIG. 2 has a 32% smaller gas recycle requirement than the conventional tubular reactor plant and a 51% smaller gas recycle requirement than a single bed adiabatic reactor plant. Hence the overall capital cost of the plant of FIG. 2 and its running costs are significantly reduced compared with the corresponding costs for the conventional forms of plant.

Vapour phase hydrogenation of n-butyraldehyde to n-butanol can be carried out in a plant which is essentially identical to that of FIG. 1. n-butyraldehyde feed is supplied to the plant via line 1 and the arrangements for vaporising n-butyraldehyde and for product recovery and gas recycle are essentially the same as in the plant of FIG. 1. However inter-cooling between successive catalytic stages 30, 31 and 32 is optional; hence items 33 to 36 and 40 to 43 can be omitted and the gas exiting catalyst bed 30 can be passed directly to bed 31 whilst the gases from bed 31 enter directly bed 32.

Although the use of n-butyraldehyde has been described, it will be apparent to the skilled reader that a mixture of n- and iso-butyraldehydes can be utilised as feed stream, for example the product aldehyde mixture produced in a propylene hydroformylation plant, particularly a rhodium-catalysed hydroformation plant operating according to the teachings of U.S. Pat. No. 3,527,809 and of British Patent Specifications Nos. 1,338,237, and 1,582,010. Moreover the teachings of the invention are equally applicable to the catalytic hydrogenation of other aldehydes, such as propionaldehyde.

FIG. 3 illustrates a further form of aldehyde hydrogenation plant. In this plant n-butyraldehyde is supplied by way of line 101 to a spray nozzle 102 mounted in a first vaporiser column 103 which is maintained at about 10.5 kg/cm$^2$ absolute (about 150 psia) and is provided with a distribution tray 104. Make up hydrogen containing gas is supplied to the plant by way of line 105 and is mixed with recycle gas in line 106 before passing on by way of line 107 to heat exchanger 108 in which it is preheated to 130° C. by indirect heat exchange with hot reaction product mixture in line 109. The resulting preheated hydrogen-containing gas is then fed through line 110 to sparger 111 in vaporiser 103. The upflowing gas in vaporiser 102 heats and vaporises the aldehyde spray from nozzle 102.

A vaporous mixture of n-butyraldehyde vapour and hydrogen-containing gas, comprising a 26:1 H$_2$:aldehyde molar ratio mixture plus inerts at a temperature of 87° C., is removed from vaporiser 103 by way of line 112. This is heated to 125° C. by passage through heater 113 which is supplied with a suitable heating medium by way of line 114. The hot mixture flows on in line 115 to first catalytic stage 116 which contains a charge of aldehyde hydrogenation catalyst, for example, a catalyst of the type described in European Patent Publication No. 0 008 767. Hydrogenation occurs substantially quantitatively and adiabatically in first catalytic stage 116. The resulting reaction mixture exits first catalytic stage 116 by way of line 117 at a temperature of 195° C. and is cooled to 150° C. in cooling stage 118, which is supplied with a suitable cooling medium in line 119. The partially cooled mixture flows on by way of line 120 to sparger 121 in second vaporiser 122.

Further n-butyraldehyde is supplied to nozzle 123 in second vaporiser 122 by way of line 124. Reference numeral 125 indicates a distribution tray. A hot vaporous mixture comprising unreacted hydrogen from first catalytic stage 116, product n-butanol, inerts, and a minor amount of by-products, e.g. n-butyl n-butyrate, also formed in first catalytic stage 116, exits vaporiser 122 overhead in line 126 at a temperature of 105° C. After passage through a heater 127, supplied with a suitable heating medium, e.g. steam, in line 128, the mixture passes on in line 129 at a temperature of 125° C. to second catalytic stage 130. The aldehyde is quantitatively hydrogenated, n-butanol being the major product, under adiabatic conditions. The temperature of the vaporous reaction mixture exiting second catalytic stage 130 in line 131 is 195° C. After heat recovery in heat exchanger 132 by indirect heat exchange with a cooling medium, e.g. boiler feed water, supplied in line 133, the reaction mixture, now at 150° C. passes on in line 109 to heat exchanger 108.

From heat exchanger 108 the cooled reaction mixture passes in line 134 to condenser 135, which is supplied with cooling water or other suitable cooling medium in line 136. The resulting gas/condensate mixture flows on in line 137 to knock out pot 138 from which crude n-butanol product is recovered in line 139. Uncondensed gases, i.e. a mixture comprising hydrogen and inerts, exit knock out pot 138 in line 140 at 40° C. and are re-compressed in compressor-circulator 141, the exit end of which is connected to line 106. A purge stream is taken from the recycle gas in line 142 in order to control the level of inerts in the circulating gas stream.

The hydrogen:aldehyde molar ratio in the vaporous mixture is controlled, by suitable adjustment of the rate of supply of n-butyraldehyde in line 124, to a preselected value, e.g. 20:1. In each case the hydrogen:aldehyde ratio and the inlet temperature to the catalytic stage determine the exit temperature from the catalytic stages 116 and 130.

Provision may be made to pump any liquid n-butyraldehyde collecting at the bottom of vaporiser 102 to a nozzle 143 by way of line 144, pump 145, line 146, heater 147 (supplied with steam or other suitable heating medium in line 148) and line 149. A similar arrangement consisting of nozzle 150, line 151, pump 152, line 153, heater 154 (with its supply line 155) and line 156, may be provided for second vaporiser 122.

It will be appreciated by those skilled in the art that FIGS. 1 to 3 are diagrammatic and that further items of equipment such as temperature and pressure sensors, pressure relief valves, control valves, level controllers and the like would additionally be required in a commercial plant. The provision of such ancillary items of equipment forms no part of the present invention and would be in accordance with conventional chemical engineering practice. Moreover it is not intended that the scope of the invention should be limited in any way by the precise methods of cooling, heating and vaporising the various process streams, or by the arrangement of coolers, heaters, heat exchangers and vaporising apparatus provided therefor, illustrated in any of FIGS. 1 to 3; any other suitable arrangement of equipment fulfilling the requirements of the invention may be used in place of the illustrated arrangements in accordance with conventional chemical engineering techniques.

What is claimed is:

1. A process for hydrogenating an aldehyde to a corresponding alcohol which comprises providing a plurality of adiabatically operated catalytic stages arranged one after another, including a first catalytic stage and one or more other catalytic stages including a final catalytic stage, each catalytic stage containing a charge of a hydrogenation catalyst effective for vapour phase catalytic hydrogenation of aldehydes, supplying to the first catalytic stage at a temperature at least as high as the threshold temperature for the hydrogenation reaction a first vaporous mixture comprising vaporous aldehyde and excess hydrogen, allowing catalytic hydrogenation to occur substantially adiabatically in the first catalytic stage so as to convert to corresponding alcohol substantially all aldehyde supplied to the first catalytic stage, supplying to the, or to each, other catalytic stage a vaporous mixture comprising (a) a substantially aldehyde free intermediate product mixture comprising unreacted hydrogen and corresponding alcohol recovered from the preceding catalytic stage and (b) supplementary vaporous material that is richer in aldehyde than the first vaporous mixture and is selected from vaporous aldehyde and mixtures of vaporous aldehyde with hydrogen at a hydrogen:aldehyde molar ratio less than that of the first vaporous mixture, the vaporous mixture supplied to the, or to each, other catalytic stage being in each case at a temperature at least as high as the threshold temperature for the hydrogenation reaction, allowing catalytic hydrogenation to occur substantially adiabatically in the, or in each, other catalytic stage, thereby to convert to corresponding alcohol substantially all aldehyde supplied to that stage, and recovering from the final catalytic stage a substantially aldehyde-free vaporous reaction mixture containing corresponding alcohol.

2. A process according to claim 1, in which the vaporous mixture supplied to the, or to each, other catalytic stage further comprises additional hydrogen.

3. A process according to claim 1, in which the hydrogen:aldehyde molar ratio of the first vaporous mixture is selected to lie within the range of from about 5:1 to about 75:1.

4. A process according to claim 1, in which the vaporous mixture supplied to the, or to each, other catalytic stage is formed by admixture of unreacted hydrogen and corresponding alcohol recovered from the preceding catalytic stage with a supplementary mixture comprising further hydrogen and vaporous aldehyde, the supplementary mixture having a hydrogen:aldehyde ratio which is less than the hydrogen:aldehyde ratio of the first vaporous mixture.

5. A process according to claim 1, in which the aldehyde contains from 1 to about 20 carbon atoms.

6. A process according to claim 5, in which the aldehyde in propionaldehyde.

7. A process according to claim 5, in which the aldehyde is selected from n-butyraldehyde, iso-butyraldehyde, and mixtures thereof.

8. A process according to claim 5, in which the aldehyde is 2-ethylpropylacrolein.

9. A process according to claim 1, in which the pressure ranges from about 1 kg/cm$^2$ absolute up to about 21 kg/cm$^2$ absolute.

10. A process according to claim 1, in which the catalyst comprises a reduced mixture of CuO and ZnO, in which the inlet temperature to each catalytic stage lies in the range of from about 100° C. to about 180° C., and in which the exit temperature from each catalytic stage does not exceed about 230° C.

11. A process according to claim 1, in which the catalyst comprises nickel.

12. A process according to claim 1, in which unreacted hydrogen recovered from the final catalytic stage is recycled to the inlet end of the first catalytic stage.

13. A process for vapour phase hydrogenation of an aldehyde to the corresponding alcohol which comprises providing a catalytic hydrogenation zone comprising n catalytic stages in series, where n is an integer of at least 2, each catalytic stage containing a charge of hydrogenation catalyst effective for vapour phase catalytic hydrogenation of aldehydes, supplying to the first catalytic stage a first vaporous mixture comprising excess hydrogen and the aldehyde at a first predetermined hydrogen-aldehyde molar ratio and at a first temperature which is equal to, or is in excess of, the threshold temperature for the hydrogenation catalyst thereof, allowing catalytic hydrogenation to occur substantially adiabatically in each catalytic stage, thereby to effect hydrogenation to corresponding alcohol of substantially all aldehyde supplied to that stage, supplying substantially aldehyde free vaporous product mixture from the, or from each, mth catalytic stage in the series, where m is an integer equal to or less than (n−1), to the corresponding (m+1)th catalytic stage in the series, supplying also to the, or to each, (m+1)th catalytic stage further vaporous material that is richer in aldehyde than the first vaporous mixture and is selected from vaporous aldehyde and mixtures of vaporous aldehyde and hydrogen having a hydrogen:aldehyde molar ratio that is less than the first predetermined ratio so as to form, together with the vaporous product mixture from the mth catalytic stage, a vaporous mixture having a predetermined hydrogen:aldehyde molar ratio which may be the same as, or may be different from, the first predetermined ratio or the corresponding molar ratio for the vaporous mixture supplied to any other stage, controlling the inlet temperature to the, or to each, (m+1)th catalytic stage to a predetermined temperature which is equal to, or is in excess of, the threshold temperature for the catalyst, and recovering from the nth catalytic stage a substantially aldehyde-free final vaporous product mixture containing the corresponding alcohol.

14. A process according to claim 13, in which n is an integer of from 2 to 6 inclusive.

15. A process according to claim 13, in which the vaporous mixture supplied to the, or to each, (m+1)th catalytic stage further comprises additional hydrogen.

16. A process according to claim 13, in which the first predetermined hydrogen:aldehyde molar ratio is selected to lie within the range of from about 5:1 to about 75:1.

17. A process according to claim 13, in which the vaporous mixture supplied to the, or to each, (m+1)th catalytic stage is formed by admixture of unreacted hydrogen and corresponding alcohol recovered from the mth catalytic stage with a supplementary mixture comprising further hydrogen and vaporous aldehyde, the supplementary mixture having a hydrogen:aldehyde ratio which is less than the first predetermined ratio.

18. A process according to claim 13, in which the aldehyde contains from 1 to about 20 carbon atoms.

19. A process according to claim 18, in which the aldehyde is propionaldehyde.

20. A process according to claim 18, in which the aldehyde is selected from n-butyraldehyde, iso-butyraldehyde and mixtures thereof.

21. A process according to claim 18, in which the aldehyde is 2-ethylpropylacrolein.

22. A process according to claim 13, in which the pressure ranges from about 1 kg/cm$^2$ absolute up to about 21 kg/cm$^2$ absolute.

23. A process according to claim 13, in which the catalyst comprises a reduced mixture of CuO and ZnO, in which the inlet temperature to each catalytic stage lies in the range of from about 100° C. to about 180° C., and in which the exit temperature from each catalytic stage does not exceed about 230° C.

24. A process according to claim 13, in which the catalyst comprises nickel.

25. A process according to claim 13, in which unreacted hydrogen recovered from the nth catalytic stage is recycled to the inlet end of the first catalytic stage.

26. A process for hydrogenating an aldehyde to a corresponding alcohol which comprises providing a catalytic hydrogenation zone comprising first, second and third catalytic stages in series, each catalytic stage containing a charge of a hydrogenation catalyst effective for vapour phase catalytic hydrogenation of aldehydes, supplying to the first catalytic stage a first vaporous mixture comprising excess hydrogen and the aldehyde at a first predetermined molar ratio at a first inlet temperature which is equal to, or is in excess of, the threshold temperature for the hydrogenation catalyst, allowing catalytic hydrogenation to occur substantially completely and substantially adiabatically in the first catalytic stage, supplying substantially aldehyde free first product mixture comprising corresponding alcohol and unreacted hydrogen from the first catalytic stage to the second catalytic stage, supplying also to the second catalytic stage further vaporous material that is richer in aldehyde than the first vaporous mixture and is selected from vaporous aldehyde and mixtures of vaporous aldehyde and hydrogen having a hydrogen:aldehyde molar ratio which is less than the first predetermined molar ratio, so as to form, together with the first product mixture, a second vaporous mixture containing hydrogen and vaporous aldehyde and having a predetermined second hydrogen:aldehyde molar ratio which may be equal to, or may be different from, the first ratio, controlling the inlet temperature to the second catalytic stage to a predetermined temperature which is equal to, or is in excess of, the threshold temperature of the catalyst, allowing catalytic hydrogenation to occur substantially completely and substantially adiabatically in the second catalytic stage, supplying substantially aldehyde free second product mixture comprising corresponding alcohol and unreacted hydrogen from the second catalytic stage to the third catalytic stage, supplying also to the third catalytic stage further vaporous material that is richer in aldehyde than the first vaporous mixture and is selected from vaporous aldehyde and mixtures of vaporous aldehyde and hydrogen having a hydrogen:aldehyde molar ratio which is less than the first predetermined molar ratio so as to form together with the second product mixture, a third vaporous mixture containing hydrogen and vaporous aldehyde and having a predetermined third hydrogen:aldehyde molar ratio which may be equal to, or may be different from, the first and/or second ratios, controlling the inlet temperature to the third catalytic stage to a predetermined temperature equal to or in excess of the threshold temperature of the catalyst, allowing catalytic hydrogenation to occur substantially completely and substantially adiabatically in the third catalytic stage, and recovering from the third catalytic stage a substantially aldehyde free third product mixture containing the corresponding alcohol.

27. A process according to claim 26, in which the vaporous mixture supplied to second and third catalytic stages further comprises additional hydrogen in each case.

28. A process according to claim 26, in which the first predetermined hydrogen:aldehyde molar ratio is selected to lie within the range of from about 5:1 to about 75:1.

29. A process according to claim 26, in which the vaporous mixture supplied to the second and third catalytic stages comprises in each case, in addition to unreacted hydrogen and corresponding alcohol recovered from the preceding catalytic stage, a supplementary mixture comprising further hydrogen and vaporous aldehyde at a hydrogen:aldehyde ratio which is less than the first predetermined ratio.

30. A process according to claim 26, in which the aldehyde contains from 2 to about 12 carbon atoms.

31. A process according to claim 30, in which the aldehyde is propionaldehyde.

32. A process according to claim 30 in which the aldehyde is selected from n-butyraldehyde, isobutyraldehyde and mixtures thereof.

33. A process according to claim 30, in which the aldehyde is 2-ethylproplyacrolein.

34. A process according to claim 26, in which the pressure ranges from about 1 kg/cm$^2$ absolute up to about 21 kg/cm$^2$ absolute.

35. A process according to claim 26, in which the catalyst comprises a reduced mixture of CuO and ZnO, in which the inlet temperature to each catalytic stage lies in the range of from about 100° C. to about 180° C., and in which the exit temperature from each catalytic stage does not exceed about 230° C.

36. A process according to claim 26, in which the catalyst comprises nickel.

37. A process according to claim 26, in which the unreacted hydrogen recovered from the third catalytic stage is recycled to the inlet end of the first catalytic stage.

* * * * *